United States Patent [19]
Wang et al.

[11] Patent Number: 5,837,468
[45] Date of Patent: Nov. 17, 1998

[54] PCR-BASED CDNA SUBSTRACTIVE CLONING METHOD

[75] Inventors: Xun Wang, Urbandale; Jonathan P. Duvick; Steven P. Briggs, both of Des Moines, all of Iowa

[73] Assignee: Pioneer Hi-Bred International, Inc., Johnston, Iowa

[21] Appl. No.: 858,767

[22] Filed: May 19, 1997

Related U.S. Application Data

[63] Continuation of Ser. No. 481,687, Jun. 7, 1995, abandoned.
[51] Int. Cl.$^6$ .............................. C12Q 1/68; C12P 19/34; C12N 15/00
[52] U.S. Cl. .............................. 435/6; 935/91.2; 935/76; 935/77; 935/78
[58] Field of Search ................... 435/6, 91.2; 935/76, 935/77, 78

[56] References Cited

U.S. PATENT DOCUMENTS

| | | | |
|---|---|---|---|
| 5,482,845 | 1/1996 | Soares et al. ........................... | 435/91.1 |
| 5,525,471 | 6/1996 | Zeng et al. ................................. | 435/6 |
| 5,629,179 | 5/1997 | Mierendorf et al. ................... | 435/91.2 |
| 5,643,761 | 7/1997 | Fisher et al. ........................... | 435/91.1 |

FOREIGN PATENT DOCUMENTS

WO 89/12695   12/1989   WIPO .

OTHER PUBLICATIONS

Frohman et al. PNAS vol. 85 : pp. 8998–9002 (1988).
Luk'Tanov et al. "Highly Efficient Subtractive Hybridization of cDNA", *J. Bioorganic Chem.*, 20(6): 386–388 (Jan. 1, 1994).
BORSON et al., "A Lock–Docking Oligo(dT) Primer for 5' and 3+ RACE PCR", *PCR Methods And Applications*, vol. 2:144–148, (1992).
LISITSYN et al., "Cloning The Differences Between Two Complex Genomes", *Science*, vol. 259:946–951, 1993.
LIANG et al., "Distribution And Cloning of Eukaryotic mRNAs By Means of Differential Display: Refinements And Optimization", *Nucleic Acids Research*, vol. 21, No. 14, pp. 3269–3275, (1993).
FROHMAN, "Race: Rapid Amplification Of cDNA Ends", *PCR Protocols, A Guide To Methods and Applications*, pp. 28–38, (Academic Press 1990).
BELYAVSKY et al., "PCR–based cDNA Library Construction: General cDNA Libraries At The Level of a Few Cells", *Nucleic Acids Research*, vol. 17:2919–2932, (1989).

Primary Examiner—W. Gary Jones
Assistant Examiner—Ethan Whisenant
Attorney, Agent, or Firm—Bell Seltzer Intellectual Property Law Group of Alston & Bird LLP

[57] ABSTRACT

A process is described in which PCR-based cDNA libraries with anchored ends are made, a PCR-based cDNA subtracted (PCSUB) library is produced therefrom, and the ends of a cDNA clone are isolated, via PCR, from an anchored-ends library.

4 Claims, 11 Drawing Sheets

A simple PCR based method for generation of a cDNA library with anchored ends

PCR Based cDNA Subtractive (PCSUB) Library

Isolation of cDNA ends from an "anchored" library (ICEFAL)

Tester and Driver RNA Preparation

Tester (+) and driver (-) dC-cDNAs were amplified with BamT17V and BamG13H primers at different magnesium concentration. The resulting DNA was analyzed by gel electrophoresis and Southern analysis. Southern results indicated [Mg2+] > 2.5mM was preferable for amplification of both MPI and ACT DNA dot-blot analysis with probes MPI and ACT.

sub 1 cDNA = subtractive cDNA obtained after the first cycle of subtraction sub 2 cDNA = subtractive cDNA obtained after the second cycle of subtraction Northern Analysis probed with cDNAs from the Subtractive cDNA library

Figure 8

Nucleic acid sequence of clone C-11-3 and the deduced amino acid sequence in a putative open reading frame

```
  1 GGATCCTGGGGGGGGGGGGACGAACTCTCTCTATACTCTCCCATCAATCCTTAAATTATC  60

61 ACGCATTATGCGAACTGTTGCAGTACTCGCTCTCTTTGCCCAACTGGCGACGTGCGCCAT 120
           M  R  T  V  A  V  L  A  L  F  A  Q  L  A  T  C  A  I -

121 ATTCAACATCACAGGATCGTGCGCCGACAGCGAAAACGGCCCTGTTTGCGTCATTACGAA 180
     F  N  I  T  G  S  C  A  D  S  E  N  G  P  V  C  V  I  T  K -

181 GAGTGTAGTTAACCCAGCTACAGTTTGCAACGGGAAGGCTGAGGCGTATGCAGGAGACGG 240
     S  V  V  N  P  A  T  V  C  N  G  K  A  E  A  Y  A  G  D  G -

241 GAATCAATGGCATGACGGGCTGTACTGGAATTGGTTCCCCTTGCACTTATGTTTGGCGAT 300
     N  Q  W  H  D  G  L  Y  W  N  W  F  P  L  H  L  C  L  A  M -

301 GCTAGACGTTCTTCCTCAACATCAAACTGCGAAGACACTGAATTCGCTTTCGGACCTTGG 360
     L  D  V  L  P  Q  H  Q  T  A  K  T  L  N  S  L  S  D  L  G -

361 TATATAATCAGCTGCAGGTCCTGGCCTACTCCCTGTTCAACTAAAAGCAACATTGCTTTC 420
     I  *

421 GTTTGTCTTCCTGTATTACCATCAATCAGAATTAACATACTCATCTCTTAAAAAAAAAAA 480

481 AAAAAA
```

Figure 9

Nucleic acid sequence of clone G-4-5 and the
deduced amino acid sequence in three reading frames.
A putative open reading frame was underlined

```
     91 GTGGATCCTTCGACGACTACCGCATGTACATCCGCCGCAAGGGGCCTCGCGGGAAGAGCC 150
a       V D P S T T T A C T S A A R G L A G R A   -
b       W I L R R L P H V H P P Q G A S R E E P   -
c       G S F D D Y R M Y I R R K G P R G K S Q   -

151 AGGTCGACTCCCTCAAGGTCGCCGACGCCGACGGCAGACAGTGCTACTAGCTAGTATATA 210
a       R S T P S R S P T P T A D S A T S * Y I   -
b       G R L P Q G R R R R R Q T V L L A S I Y   -
c       V D S L K V A D A D G R Q C Y * L V Y T   -

211 CCTAGCCAGCCTGCTGCCGATCGAGATTGTTTGTATGTGTGGTGTGTGCATGCATTTGCC 270
a       P S Q P A A D R D C L Y V W C V H A F A   -
b       L A S L L P I E I V C M C G V C M H L P   -
c       * P A C C R S R L F V C V V C A C I C P   -

271 CACACTGACCACTGTCCACATGTACGCCGCCAGCTGCCGGCCCTAAATAAAACCATGCAT 330
a       H T D H C P H V R R Q L P A L N K T M H   -
b       T L T T V H M Y A A S C R P * I K P C I   -
c       H * P L S T C T P P A A G P K * N H A *   -

331 AGATTAGCTAGCTTATGATTAATCAAGTCTTAGCAGCTAGAGAGTGCTTTGGGTTGGGAC 390
a       R L A S L * L I K S * Q L E S A L G W D   -
b       D * L A Y D * S S L S S * R V L W V G T   -
c       I S * L M I N Q V L A A R E C F G L G L   -

391 TCTCTCATAGGAGGGNATGCTTGATCGATCCGATCATCAATTTGAAACACCCTGCTAGGT 450
a       S L I G G ? A * S I R S S I * N T L L G   -
b       L S * E G M L D R S D H Q F E T P C * V   -
c       S H R R ? C L I D P I I N L K H P A R L   -

451 TGTGCANCTCCGCCGTCCAANCCACAAAGGGGNGANGTCAANTGAAGGGTGAGANAACGT 510
a       C A ? P P S ? P Q R G ? V ? * R V R ? R   -
b       V ? L R R P ? H K G ? ? S ? E G * ? N V   -
c       C ? S A V Q ? T K G ? ? Q ? K G E ? T S   -

511 CAANAACGAAGCNAGCTAGTTCCCNTTATTNGGGTGGTTCTCAAAAAAAAA 561
a       Q ? R S ? L V ? ? I ? V V L K K K   -
b       ? N E A S * F P L ? G W F S K K     -
c       ? T K ? A S S ? Y ? G G S Q K K     -
```

Figure 10

Comparison of the amino acid sequence deduced from the nucleotide sequence of clone G-12-3 with the sequences of known cytochrome P450 proteins. Asterisk indicates the identical amino acids shared among these sequences

```
         451                                                              500
B34181   ERYNPQRWLD  IRGSGRNFHH  .VPFGFGMRQ  CLGRRLAEVE  MLLLLHHVLK
A37088   ERYNPQRWLD  IRGSGRNFHH  .VPFGFGMRQ  CLGRRLAEAE  MLLLLHHVLK
A31418   EKFDPGHFLN  ANGTFRKSNY  FMPFSAGKRI  CAGEGLARME  LFLFLTSILQ
A24814   EKFDPGHFLN  ANGTFRRSDY  FMPFSAGKRI  CAGEGLARME  IFLFLTSILQ
04hua6   QDFNPQHFLN  EKGQFKKSDA  FVPFSIGKRN  CFGEGLARME  LFLFFTTVMQ
S19657   ETFKPEHFLN  ENGKFKYSDY  FKAFSAGKRV  CVGEGLARME  LFLLLSAILQ
G-12-3   EKFIPERWLN  ETPEMKSA..  LTPFSLGKRN  CIGQNLAWQE  LYWAVNEVMR
              *   *                 *  * *    *  *  **   *

501                                        541
B34181   HF..LVETLT  QEDIKMVYSF  ILRPGTSPLL  TFRAIN..... .
A37088   HF..LVETLT  QEDIKMVYSF  ILRPGTSPLL  TFRAIN..... .
A31418   NFS.LKPVKD  RKDIDISPIV  TSAANIPRPY  EVSFIPR... .
A24814   NFS.LKPVKD  RKDIDISPII  TSLANMPRPY  EVSFIPR... .
04hua6   NFR.LKSSQS  PKDIDVSPKH  VGFATIPRNY  TMSFLPR... .
S19657   HFN.LKSLVD  PKDIDLSPVT  IGFGSIPREF  VICVIPRS.. .
G-12-3   SGSRFRVAEE  MKDWEME.ME  DRFNIAPRGR  RLMLTASQVN
                         *
```

```
B34181: human cytochrome P450 11B1
A37088: human cytochrome P450 11B2
A31418: chicken cytochrome P450 2F2
A24814: chicken cytochrome P450 phenobarbital-
        inducible
04hua6: human cytochrome P450 2A6
S19657: mouse cytochrome P450 2E1
G-12-3: maize putative cytochrome P450
```

Isolation of the 5'-end of cDNA G-12-3 clone by ICEFAL technique. PCR with GSP1 and BamG13H primers resulted in an amplification of a 1.6kb DNA fragment from tester cDNA library. Single primer controls did not result in amplification of this fragment.
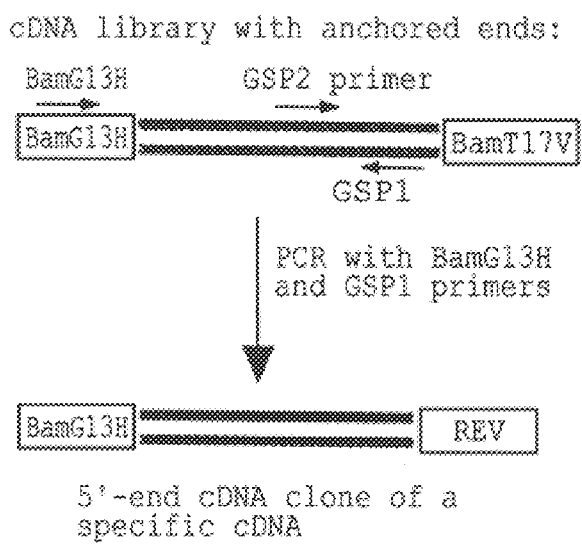
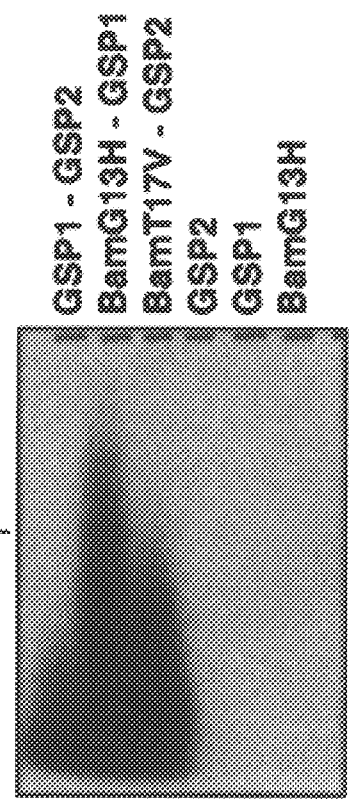
Figure 11A                              Figure 11B

PCR-BASED CDNA SUBSTRACTIVE CLONING METHOD

BACKGROUND OF THE INVENTION

This application is a continuation of application Ser. No. 08/481,687, filed Jun. 7, 1995 now abandoned.

Polymerase chain reaction (PCR) technology is employed in a growing variety of ways, including preparation of cDNA's and constructing cDNA libraries. An early use of PCR to generate a cDNA library was reported by Belyavsky et al., *Nucleic Acids Res.* 17: 2919–32 (1989).

The Belyavsky method utilized oligo (dT) as a primer for reverse transcriptase reaction, followed by poly (dG) tailing via the action of terminal deoxynucleotidyl transferase (TdT). The resulting dG-tailed cDNAs were subsequently amplified with poly (dT) and poly (dC) primers. The cDNA pool thus obtained was cloned into a vector for subsequent cDNA screening.

Since an oligo (dT) primer can anneal at any position of the poly(A) tail of a (+) strand of cDNA, and an oligo (dC) primer can anneal at any position of the poly(G) tail of a (−) strand of cDNA, the amplified cDNAs generated by the Belyavsky method often have varying lengths. Accordingly, these products cannot be analyzed directly, and instead require subcloning and screening of a cDNA library, a time-consuming technique. Furthermore, the use of primers containing homopolymers on the 3' end typically yields a high background of non-specific product.

A technique for rapid amplification of cDNA ends (RACE) was described by M. A. Frohman and his colleagues. See Frohman et al., *Proc. Nat'l Acad. Sci. USA* 85: 8998–9002 (1988), and Frohman, PCR PROTOCOLS, A GUIDE TO METHODS AND APPLICATIONS 28–38 (Academic Press 1990). The RACE protocol produces specific cDNAs by using PCR to amplify the region between a single point on a transcript and the 3' or the 5' ends. One requires knowledge of the sequence of an internal portion of the transcript, however, in order to design a primer for use in conjunction with either the polyT or polyG primers to amplify the ends. This protocol therefore yields specific cDNAs products only, not whole libraries.

A modification to the RACE protocol introduced by Borson et al., *PCR Methods and Applications* 2: 144–48 (1992), entails the use of a "lock-docking oligo (dT)." The locking mechanism involves extending the poly dT primer, by either one nucleotide (A, C or G) or by two nucleotides (also A, C or G) and yet one more of the four possible nucleotides, at the 3'-end of the primer. This "locks" the primer to the beginning of the poly dT tail, either the natural dT or a poly dT tail attached to the first strand cDNA 3'-end, by use of TdT, resulting in the synthesis of cDNA's of discrete lengths. Subcloning and screening of subclone library is not necessary before analysis, which can speed up the inquiry. Like the RACE protocol, however, Borson's protocol uses a gene-specific internal primer and, hence, produces only specific cDNAs, not whole libraries.

Approaches are described in the literature to identify mRNA expressed differentially, either in only some cell types, or at certain times of a biological process, or during infection by a parasite or a virus, etc. Those studies generally employ subtractive hybridization to reveal the differentially expressed mRNA(s). Liang and colleagues have used the anchored-end technique to look for specific differences in mRNA populations. Liang et al., *Nucleic Acids Res.* 21: 3269–75 (1993). The Liang method, called "differential display," employs a decanucleotide of arbitrary sequence as a primer for PCR, internal to the mRNA, and a polyTMN primer on the 3'-end of mRNAs; "M" in this context is randomly G, C or A, but N is chosen as one of the four possible nucleotides. When such sets of primers are employed, patterns of mRNAs can be visualized, upon polyacrylamide gel electrophoresis of the PCR product, and the comparison of such patterns produced by mRNAs from two sources reveal the differentially expressed mRNAs.

The differential display method can identify individual, differently expressed mRNA's, but cannot constitute a complete library of such mRNA's. As a further consequence of having one primer of an arbitrary sequence, and therefore probably not having an exact match, low copy number mRNAs may not be picked up by this method. Finally, the cDNA candidates identified would still require recovery from the gel and subcloning, if the individual cDNA is desired for further analysis.

Lisitsyn et al., *Science* 259: 946–51 (1993), have described a representational differences analysis (RDA) method which uses subtractive hybridization and PCR technology to define the differences between two genomes. Like other subtractive hybridization protocols, in RDA there are defined two sets of DNAs, the "tester" DNA and the "driver" DNA. According to the RDA protocol, the DNA of the two genomes to be compared are digested by restriction endonucleases, and a dephoshorylated double-stranded oligonucleotide adapter is ligated. After denaturation and hybridization of driver and tester DNA, oligonucleotides from the adaptors covalently linked to tester DNA were used to amplify unique DNA sequences of tester library. The adapters are partially double-stranded DNAs made by partially complementary oligos, where the single-stranded sequence at one end of the double stranded adapter is complementary to the single-strand tail of the digested genomic DNA. The combined use of (i) restriction enzyme-digested DNA as PCR substrate and (ii) the preferential amplification of shorter substrates results in a population of fairly short, amplified DNA molecules. The adapters then are removed by cleavage with the restriction enzymes used originally to digest the DNA. To the tester DNA, new adapters with novel sequences are ligated, the tester and driver DNA are mixed, the DNA strands are separated by heating ("melting"), and the DNA's are cooled to allow for reannealing. PCR is performed with primers complementary to the adapters on tester DNA, thereby amplifying only target DNA, i.e., only DNA unique to the tester DNA. By restriction enzyme digestion of the adapters from the amplified DNA and ligation of additional, novel adapters, followed by PCR, the target DNA is amplified to become the dominant fraction.

The RDA procedure does not use any physical method of separation between the tester and driver DNA which, if used, would allow enhanced purification of target DNA. The method is used only to identify differences between genomes and was not used to identify differential cDNA expression.

In view of the limitations of the RACE and RDA methodologies, it would be very useful to have one method to provide full-length, anchored-ended cDNA libraries, for creation of differentially expressed cDNA libraries, and to use PCR to screen such libraries for the ends of specific mRNAs.

SUMMARY OF THE INVENTION

It therefore is an object of the present invention to provide a PCR-based method for generating a full-length cDNA library with anchored ends. The method would use lock-docking oligos as PCR primers, one primer, polyTV locking over the polyA tail of eukaryotic mRNA and producing the first strand synthesis, and a second primer, polyGH that would lock onto polyC tail added by TdT to the newly synthesized strand. This would contrast with the methods of Belyevsky and of Borson in that (a) discrete sized PCR products would result which would not necessarily require further subcloning/screening, (b) full-length cDNA's would be produced and (c) cDNA libraries would be produced as opposed to specific cDNA clones.

It is a further object of the present invention to generate a PCR-based cDNA subtractive (PCSUB) library. This would be accomplished by generating in the first place two cDNA libraries with anchored ends, one of tester DNA and one of driver DNA. The two libraries would undergo subtractive hybridization and amplification, to some extent similar to the RDA method, but with significant differences. In addition to using dephoshorylated adaptors which prevents amplification of driver DNA, we prepared a biotin-tagged driver library by use of biotin labeled dCTP during PCR. This would allow for a physical separation (using streptavidin-coated beads) of driver and of driver/tester hybrid cDNA from the desired and amplified target cDNA, thus enhanced relative amplification of target cDNA. Having a way to remove the driver cDNA also allows for use of a higher ratio of driver/tester cDNA, and therefore more stringent subtraction of cDNA sequences which are not unique to the target cDNA. More importantly, the PCSUB method, unlike RDA, would result in a library representing differentially expressed mRNAs.

It is yet a further object of the present invention to utilize PCR and sequence information derived from cDNA clones from the PCSUB library in order to screen the cDNA anchored end library for the ends of specific cDNA sequences. This approach would employ primers that are complementary to internal sequences, in conjunction with polyTV or polyGH or equivalent primers which comprise restriction enzyme recognition sequences at their respective 5'-ends, to "fish out" from the library the ends of specific mRNA's.

In accomplishing these and other objectives, there has been provided, in accordance with one aspect of the present invention, a method based on PCR for generating a cDNA library with anchored ends, comprising the steps of (A) providing an RNA preparation that comprises polyadenylated mRNA from a biological sample, the polyadenylated mRNA having a polyA portion and a non-polyA portion;

(B) preparing an oligonucleotide polyTV primer that anneals to the polyA portion of the polyadenylated mRNA, anchoring the polyTV primer such that a reverse transcriptase reaction can start within one nucleotide from the 3' end of the non-polyA portion;

(C) using the polyTV primer to generate by PCR from the RNA preparation a DNA strand that is complementary to the polyadenylated mRNA;

(D) using terminal deoxynucleotidyl transferase to add a polynucleotide tail at the 3' end of the DNA strand, whereby the DNA strand has a first portion that is complementary to the polyadenylated mRNA and a tail portion;

(E) preparing an oligonucleotide polyGH primer that anneals to the polynucleotide tail attached in step (D), anchoring the polyGH primer such that a reverse transcriptase reaction can start one nucleotide downstream from the 5' end of the first portion of the DNA strand; and then (F) using the polyGH primer and the polyTV primer to amplify the DNA strand by PCR.

In a preferred embodiment, the polynucleotide tail in step (D) is a polyC tail.

In accordance with a second aspect of the present invention, a method is provided for generating a cDNA library with anchored ends, as described above, wherein each of the polyGH primer and the polyTV primer contains a recognition site for a restriction endonuclease.

According to yet a third aspect of the present invention, there has been provided a method of comparing two cDNA libraries to identify cDNA that is unique to one of the libraries, comprising the steps of (A) preparing a first cDNA library and a second cDNA library with anchored ends, wherein the first cDNA library contains the unique cDNA and is prepared according to the aforementioned second aspect of the invention, and wherein the second cDNA library is similarly produced and incorporates biotin-labelled deoxynucleotides, and (B) digesting the first cDNA library with a restriction enzyme for which a recognition sequence is found on the polyGH and polyTV primers, to produce, at the ends of cDNAs in the first library, single-stranded DNA tails, (C) preparing multiple sets of double-stranded adapter DNA molecules, each set comprising a first and a second oligonucleotide of such sequence that:

(1) the 3' end of the first oligonucleotide complements the 5' end of the second oligonucleotide of the same set and (2) the 5' end of the first oligonucleotide complements the single-strand DNA produced by a restriction enzyme digest at the anchored ends of the first DNA library, (D) manipulating the libraries by mixing them; subjecting them to DNA-melting conditions; allowing for reannealing of DNA strands in the libraries; purifying the unique cDNA by trapping on streptavidin beads DNA that incorporates the biotin-labeled deoxynucleotides, whereby a cDNA fraction enriched for the unique cDNA is obtained; producing blunt-ended DNA by filling-in the unique cDNA ends with Klenow enzyme reactions; and subject the cDNA fraction to PCR amplification of the unique DNA via oligonucleotide primers that comprise an adapter molecule used in step (D), (E) digesting the unique cDNA with the restriction enzyme and ligating an adapter set from the multiple sets to the anchored ends of the first library, and then (F) repeating steps (D) and (E), each time ligating a new set of adapter DNA molecules from the multiple sets to the cDNA fraction, until the unique cDNA is essentially free of non-unique cDNA from the first library.

Still another aspect of the present invention comprehends a method of isolating the cDNA ends of a unique cDNA from an anchored library produced pursuant to to either the second or the third aspects detailed above. This method comprises the steps of (A) providing a set of PCR primers that hybridize, respectively, to a sequence internal to the unique cDNA and (B) using the primers with the polyTV or the polyGH primers in PCR reactions to produce two ends of the cDNA, wherein the primers contain a restriction enzyme cleavage site.

Other objects, features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 8 lists the nucleic acid sequence of C-11-3 (SEQ ID NO:27), one of the *F. moniliforme* induced, plant cDNA clones from the PCSUB. An observed open reading frame (SEQ ID NO:28) is indicated.

FIG. 9 lists the nucleic acid sequence of G-4-5 (SEQ ID NO:29), one of the *F. moniliforme* induced, plant cDNA clones from the PCSUB library. The longest observed reading frame is underlined (SEQ ID NO:31).

FIG. 10 compares the amino acid sequence deduced from the nucleic acid sequence of G-12-3 (SEQ ID NO:39), a cDNA clone from the PCSUB library, with P450 proteins from other sources (SEQ ID NOS:33–38, respectively). The organism of origin for the other P450 proteins is indicated in the bottom panel.

FIG. 11 illustrates the isolation of the 5'-end of cDNA clone G-12-3 (SEQ ID NO:39) by using the ICEFAL technique. Panel A depicts schematically how primers GSP1 (SEQ ID NO:19) and BamG13H (SEQ ID NOS:16–18) are used on a cDNA library with anchored ends to amplify the 5'-end of a clone. Panel 2 shows a Southern Blot of the PCR products using the primer pairs indicated. The gel was 1.2% agarose. The probe was clone G-12-3 (SEQ ID NO:39).

DETAILED DESCRIPTION OF THE PREFERRED EMBODIMENTS

Figure 1:
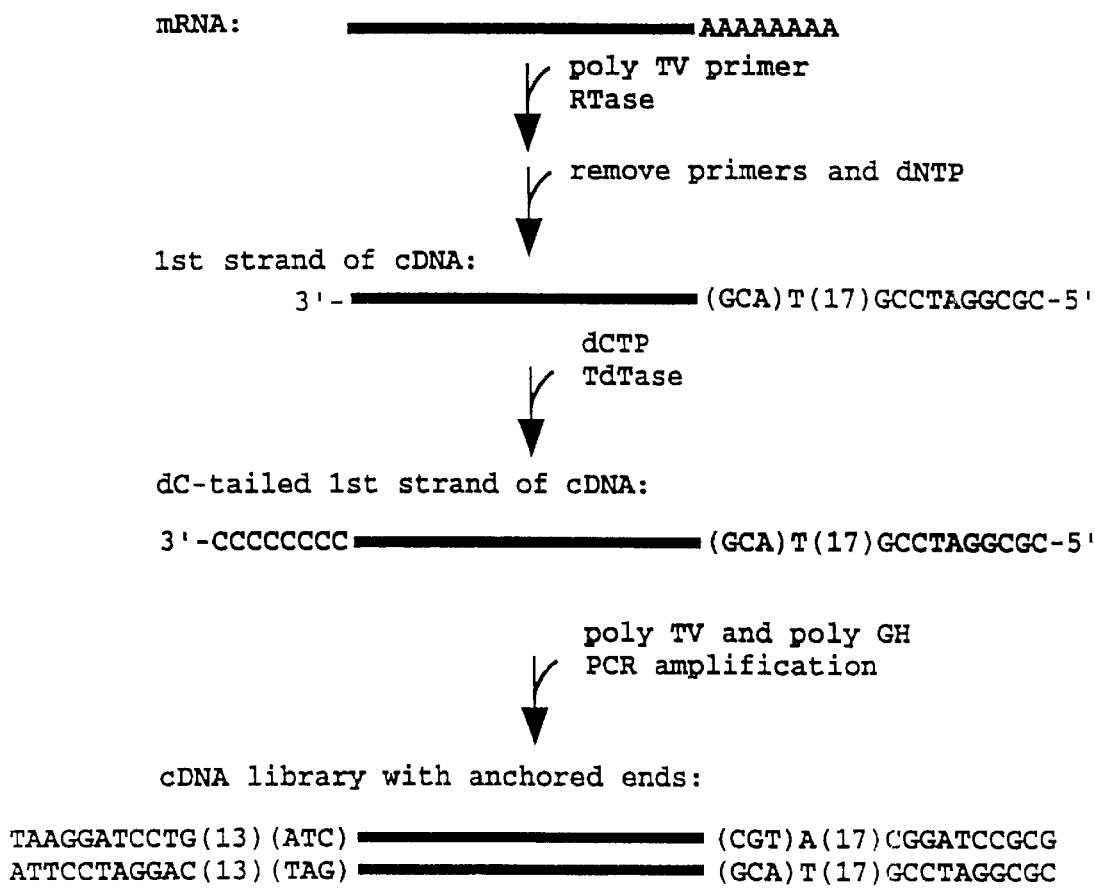
FIG. 1 depicts a general scheme using PCR to generate a cDNA library with anchored ends. As depicted, a polyTV primer anchors on the beginning of the polyA tail of the mRNA. After synthesis of the first strand (SEQ ID NOS:13–15, respectively) by reverse transcription, a polyC tail is added to the 3'-end, by use of TdT. In the last step, PCR is performed employing polyGH and polyTV to amplify the first strand and produce a cDNA library with anchored ends (SEQ ID NOS:16–18, 21–23, 24–26, and 13–15, respectively. The polyGH and polyTV primers are used here as illustrative primers.

The present invention provides a PCR-based method of creating a full-length cDNA library with anchored ends. The invention assumes that "good quality" mRNA is obtained, either as a polyadenylated fraction, or as total cellular RNA. An RNA fraction which is further enriched for mRNA containing polyA at its 3'-end is preferred, since it provides more substrate for the PCR reaction. The phrase "good quality" RNA denotes full-length, non-degraded RNA. A variety of methods for obtaining RNA, and methods to assess its quality, are known to those versed in the art, and some of those methods are described hereinafter. In accordance with the present invention, a primer for the first-strand cDNA synthesis takes advantage of the polyA tract located at the end of eukaryotic mRNA; hence, the primer consists in part of a polyT chain. But the polyT primer can typically hybridize at any point on the polyA tail of the mRNA. Primer extension by a reverse transcriptase would thus create a first strand of varying lengths, and lead eventually to a situation where one has to screen through various versions of what is basically the same cDNA, to isolate the cDNA of interest.

To eliminate this problem, the primer contains one non-A nucleotide (C, G or T) at its 3'-end. Such a primer would "lock" at the 3'-end of a mRNA, since the C, G or T nucleotide would need to hybridize to a nucleotide other than the adenine nucleotides of the polyA tail. According to the present invention, the primer described above is called "polyTV," where "V" denotes for A, C or G.

The first strand is synthesized by extension of the polyTV primer, by addition of deoxynucleotides, by a reverse transcriptase enzyme. The first strand would be purified by standard methods and a polyC tail would be added to the 3'-end of the cDNA by TdT. A polyGH primer is synthesized which, by analogy to the discussion of the polyTV primer, would lock onto the 5'-end of the cDNA. Here H stands for A, C or T. PCR reactions using the polyTV and polyGH primers would amplify the cDNA library, which then, either could be used directly for further experiments, as described hereinafter, or could be cloned into a plasmid vector. This scenario is illustrated in FIG. 1.

To a person skilled in the art, many variations on this theme are readily apparent. By way of example, but not limited to said examples, the polyTV and polyGH primers could have restriction enzyme recognition site(s) built in near the 5'-end. The restriction enzyme recognition site(s) can be the same, or different to allow for unidirectional cloning. The length of the T or G tracts can be varied. TdT can add to the 3'-end of the first strand a nucleotide other than cytosine, with corresponding complementary changes in the sequence of the primer. The PCR conditions can be optimized for the specific primers used. The polymerase enzyme used can be one of a number of polymerases used for PCR. The polymerase can incorporate labelled or modified nucleotides. In all events, a cDNA library thus produced contains full-length cDNAs, anchored at both ends by known sequences, herein referred to as an "anchored-end cDNA library."

FIG. 1 illustrates one embodiment of the invention. Here the polyTV primer has a BamHI site near the 5'-end. The polyT tract is 17 nucleotides long. This specific primer is referred to herein elsewhere as BamT17V (SEQ ID NOS:13–15). The polyGH primer also has a BamHI site near its 5'-end and has a stretch of 13 guanines. This primer is called "BamG13H" (SEQ ID NOS:16–18) elsewhere in this description.

The present invention also provides for a way to make a PCR-based cDNA subtractive (PCSUB) library. The principle is that two pools of RNA serve as substrates for separate cDNA libraries. One pool, the tester RNA, contains some mRNA(s) which are differentially expressed when compared with the mRNA of the other pool, the driver RNA. Two separate cDNA libraries are made; a tester cDNA library and a driver cDNA library. The driver cDNA library serves the purpose of subtracting from the tester cDNA library all the cDNAs which they have in common. This is accomplished by mixing aliquots of the two libraries, with the driver cDNA in large excess, say 100×, allowing for the separation of the DNA strands and reannealing, usually by heating followed by slow cooling. cDNA common to both libraries will form hybrid double stranded molecules, and, if the driver cDNA was tagged in such a manner as to allow its removal, hybrid DNA molecules also will be removed. What cDNA remains is highly enriched for target cDNA, i.e., the product of the differentially expressed RNAs. The remaining cDNA is amplified by PCR. In practice, this is best accomplished if some short stretch of double-stranded DNA molecule, called an "adapter" elsewhere in this description, is attached only to the tester cDNA molecules that remain after the subtractive hybridization step described above. One possible way to accomplish this would require that the tester cDNA library only, prior to the mixing of the libraries for the subtractive hybridization step, is digested with the restriction enzyme that has a recognition site built in on the 5'-end of the polyTV and polyGH tails. The restriction digest, by virtue of an appropriate choice of restriction enzyme/ restriction site design, will produce a cDNA with single-stranded tails.

The adapter molecule comprises two partially complementary oligonucleotide sequences, so that a single-stranded tail protrudes that is complementary to the single-stranded DNA on the ends of the tester cDNA. The adapter is ligated to the tester cDNA, usually by T4DNA ligase. One of the oligos which comprised the adapter then serves as a primer for PCR, thus amplifying the tester DNA only. For an efficient removal of tester cDNA which is not the target cDNA, multiple rounds of subtractive hybridization followed by amplification of remaining tester cDNA may be required. For this purpose the aforementioned cDNA which is enriched for target DNA again is cleaved with a restriction enzyme for which there is a recognition site on the polyTV and polyGH primers. Subtractive hybridization relative to excess driver cDNA then is carried out, using an adapter molecule of a sequence that is different from that of the adapter(s) previously employed.

Three such adapter sets are listed in the following table (SEQ ID NOS:1–12, respectively), described by Lisitsyn (Lisitsyn et al., Science 259: 946–51 (1993). The listed adapters are a subset of such adapters mentioned by Lisitsyn et al., supra.

TABLE

| Adapter Sets | | |
|---|---|---|
| adapters | name | sequence |
| 1st round | R Eam 24 | 5'-AGCACTCTCCAGCCTCTCACCGAG-3' |
| | R Bam 12 | 5'-GATCCTCGGTGA-3' |
| | after pairing | 5'-AGCACTCTCCAGCCTCTCACCGAG-3' |
| | | 3'-AGTGGCTCCTAG-5' |
| 2nd round | J Bam 24 | 5'-ACCGACGTCGACTATCCATGAACG-3' |
| | J Bam 12 | 5'-GATCCGTTCATG-3' |
| | after pairing | 5'-ACCGACGTCGACTATCCATGAACG-3' |
| | | 3'-GTACTTGCCTAG-5' |
| 3rd round | N Bam 24 | 5'-AGGCAACTGTGCTATCCGAGGGAG-3' |
| | N Bam 12 | 5'-GATCCTCCCTCG-3' |
| | after pairing | 5'-AGGCAACTGTGCTATCCGAGGGAG-3' |
| | | 3'-GCTCCCTCCTAG-5' |

The qualities of the initial tester and driver anchored ends library, and the degree of enrichment achieved after each round of subtractive hybridization/amplification, should be checked by any of the various techniques conventionally employed for this purpose. One such approach uses two cDNA clones, one for a gene known to be differentially expressed and the other for a known gene that would be represented in both the tester and driver RNA pools and cDNA libraries. These genes could be used to probe Northern blots and/or dot blots of the starting mRNAs, the cDNA libraries, and of the material after rounds of subtractive hybridization/amplification to determine (a) the quality of starting RNA (expect unique, full-length bands), (b) the quality of the cDNA libraries, and (c) that the differentially expressed mRNA is present in larger amounts after subtractive hybridization but (d) the non-differentially expressed gene is under-represented after subtractive hybridization/ amplification.

There are variations, readily apparent to one skilled in the art, to the techniques described above for the making of the PCSUB library. For example, the primers used to anchor the 5'-end of the tester cDNA library need not be the same as the respective primers for the driver cDNA library. This would eliminate the need to place adapters on the material after the first round of subtractive hybridization/amplification. The polyTV and polyGH, or equivalent primers, used to make the tester and driver libraries may have multiple cloning sites (MCS) near their 5'-ends. The tester library probably contains internal to the sequence of some of its members the restriction site used for adapter molecule attachment to the ends of the cDNA. Therefore, any one isolated clone may not be full-length. If the initial tester library had an MCS at its ends, one could use the library in order to fish out the ends of the desired clone.

Figure 2:
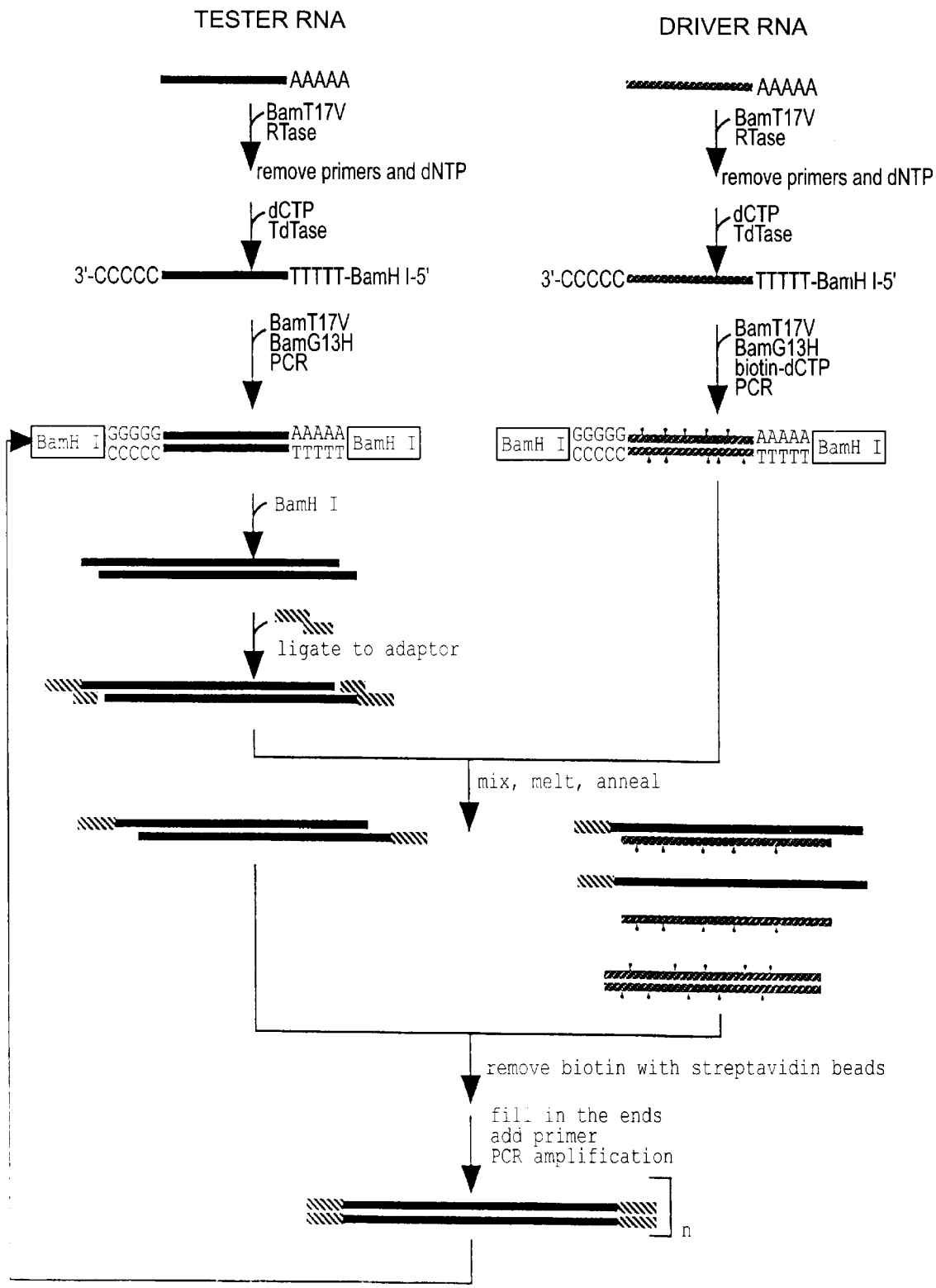
FIG. 2 details the making of a PCSUB library. The first few steps shown entail the making of two libraries, employing "tester" RNA and "driver" RNA as substrates. The libraries are constructed similarly to the description of FIG. 1. But the restriction site implicit in the 5'-end sequence of the polyTV and polyGH primers of FIG. 1 are indicated here as a BamHI site; the primers therefore are denoted "BamT17V" and "BamG13H," respectively. BamH1 is illustrative only, and other restriction enzyme recognition sequence(s) are possible. Also, an important addition to the scheme of FIG. 1 is the use of biotin-dCTP to "tag" the PCR product. In the next step the tester cDNA library is digested with the restriction enzyme(s) for which recognition sites are built in the 5'-end of the anchor, here BamHI. An adaptor DNA then is ligated to the tester cDNA library, followed by "substraction" of target cDNA from the two libraries. This is accomplished by mixing the DNA of the tester and driver libraries, the melting of the DNA molecules into simple stranded DNA, preferably by heating, and the reannealing of complementary strands by a process of slow cooling. Finally, the biotin-labeled cDNA, both from the driver library and from the tester library which "found" a complementary strand to driver library cDNA, are removed by passing through and trapping on a slurry of streptavidin beads. The ends of the DNA are made double-stranded, preferably by Taq polymerase reaction, and the mixture enhanced for target cDNA is amplified using primer(s) complementary to the adapter molecule(s). The process of producing BamHI ends, ligating adapter sets, subtracting the target cDNA from a mixture of tester and driver cDNAs, and amplifying by PCR for the target cDNA is repeated as many times as deemed necessary to get essentially pure target cDNA. Since the sequence of the adapter sets used each time is different, target cDNA is preferentially amplified each time away from remaining process of tester cDNA.

Other variations in PCR technique, in the choice of polymerase enzyme employed, in the methods applied to clean up the PCR product, and in the method used to remove the biotin tagged cDNA at the end of the subtractive hybridization step, inter alia, also are within the scope of the present invention. An embodiment of the preparation of a PCSUB library is illustrated in FIG. 2 and used in experiments described hereinafter. According to this embodiment, please refer to FIG. 2, the tester and driver cDNA libraries are made with primers BamT17V and BamG13H (SEQ ID NOS:13–15 and 16–18, respectively). The driver cDNA library is tagged by using biotin-dCTP. After the subtractive hybridization step, the biotin labeled cDNA molecules, now a mixture of driver cDNA library and of hybrid tester/driver derived cDNA molecules, are removed. The removal of the biotin labeled DNA is accomplished by trapping the biotin labeled DNA molecules on streptavidin-paramagnetic particles which next are captured on a magnetic strand (Promega Corporation, Madison Wis.). According to the embodiment, adapter sets are used to facilitate selective amplification as described above. The specific sets employed are those enumerated in the aforementioned table, used in the order which they appear there (the first set first, etc).

Figure 3:
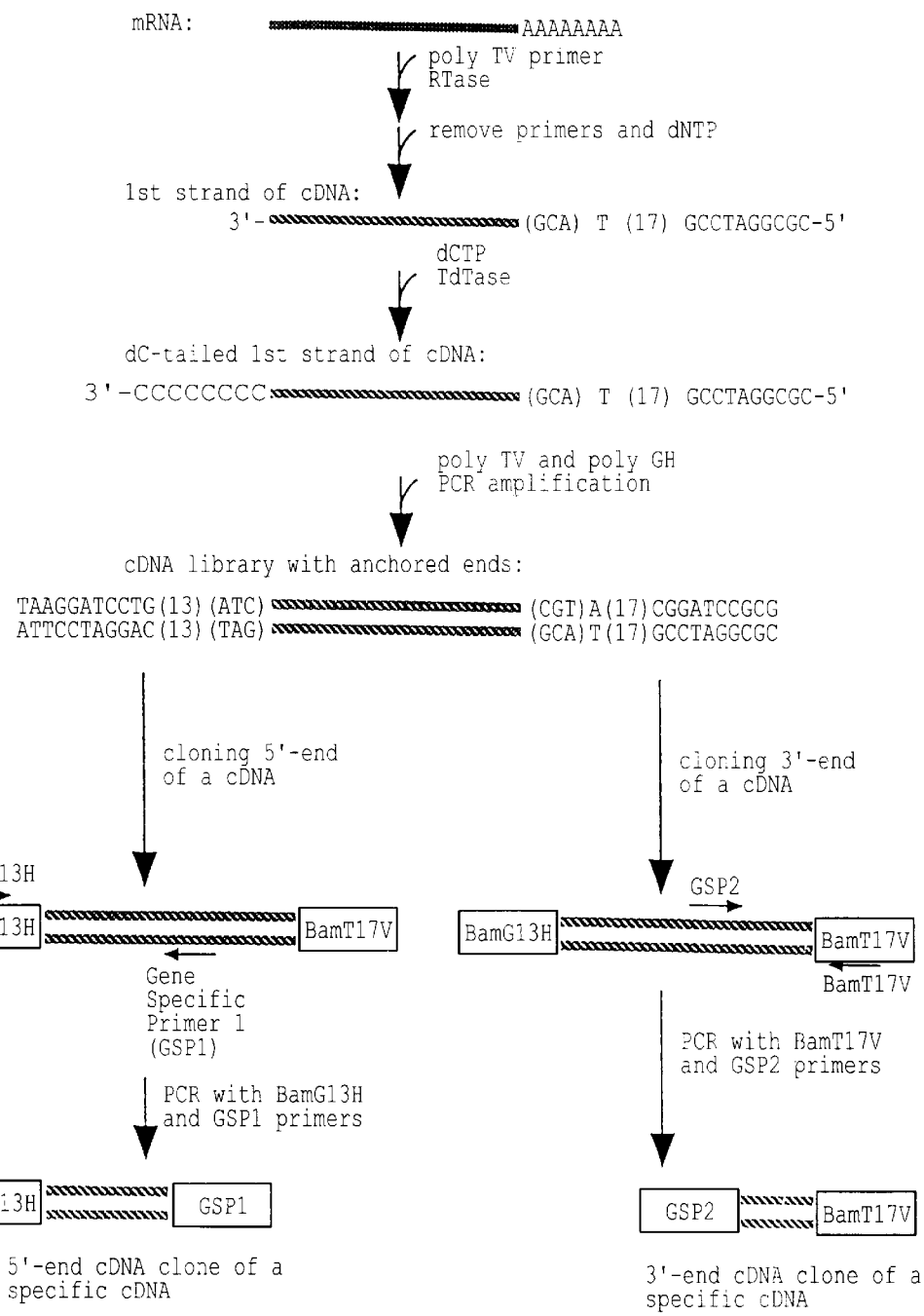
FIG. 3 portrays the isolation of cDNA ends from an anchored library (ICEFAL). The preparation of a cDNA anchored library is done as illustrated in FIG. 1. Next, gene-specific PCR primer 1, GSP1 (SEQ ID NO:19), is used together with primer BamG13H to produce a clone of the 5'-end of the desired gene, and gene-specific primer 2, GSP2 (SEQ ID NO:20), is used together with primer BamT17V to produce the 3'-end of the clone.

It is another object of the present invention to present a method of isolation of cDNA ends from an anchored library (ICEFAL). The anchored ends cDNA library is prepared as described above and recapitulated in FIG. 3. The isolation of the cDNA ends requires knowledge of the nucleic acid sequence over some internal position of the cDNA desired. Such knowledge can come from any source, not limited to the following examples: knowing the sequences of a peptide fragment, guessing the sequence by analogy with a well-preserved section of the equivalent gene from another organism, or, in line with our claims, from having isolated and analyzed clones from our PCSUB library. According to the present invention, two primers are made based on the known internal sequence, each complementary to a different strand of the cDNA. The primer that can be extended to the 5'-end of the cDNA is called "gene-specific primer 1" (GSP1) (SEQ ID NO:19), and is used in conjunction with polyGH (BamG13H (SEQ ID NOS:16–18) in FIG. 3) to amplify the 5'-end of the clone. The primer that can be extended to the 3'-end of the cDNA clone is called gene-specific primer 2 (GSP2) (SEQ ID NO:20), and in conjunction with primer polyTV (Bam17TV (SEQ ID NOS:13–15) in FIG. 3), is used to amplify the 3'end. All primers are designed with restriction site(s) near the 5'-end, which allows for subsequent cloning of the cDNA ends (see FIG. 3).

The following commentary illustrates the present invention by reference to a series of experiments. The goal of the experiments was to isolate and then analyze plant embryo genes that were induced by infection with the fungus *Fusarium moniliforme*.

Fungal infection and total RNA preparation

Maize seeds (Pioneer Hi-Bred Int'l inbred line HT1) were used as the experimental material. *Fusarium moniliforme* isolate M033 was obtained from moldy corn ears at Johnston, Iowa.

Fungal infection of germinating embryos was performed as reported by Casacuberta et al., Plant Molec. Biol. 16: 527–36 (1991). Seeds were washed with sterile water for 3 minutes followed by a wash with full strength commercial bleach (5.25% sodium hypochloride) at room temperature for 10 minutes. Then the seeds were washed three times with sterile water. After the seeds were imbibed for 4 hours, embryos were dissected from these seeds under sterile conditions. Dissected embryos were germinated on wet filter paper in the dark at 28° C. for 24 hours and then inoculated with the conidial suspension of *Fusarium moniliforme* by adding 50 μl (approximately 1000–3000 spores/ml) to each embryo. Inoculated seeds and sterile control seeds were allowed to continue germination for two more days in the dark at 28° C.

Figure 4:
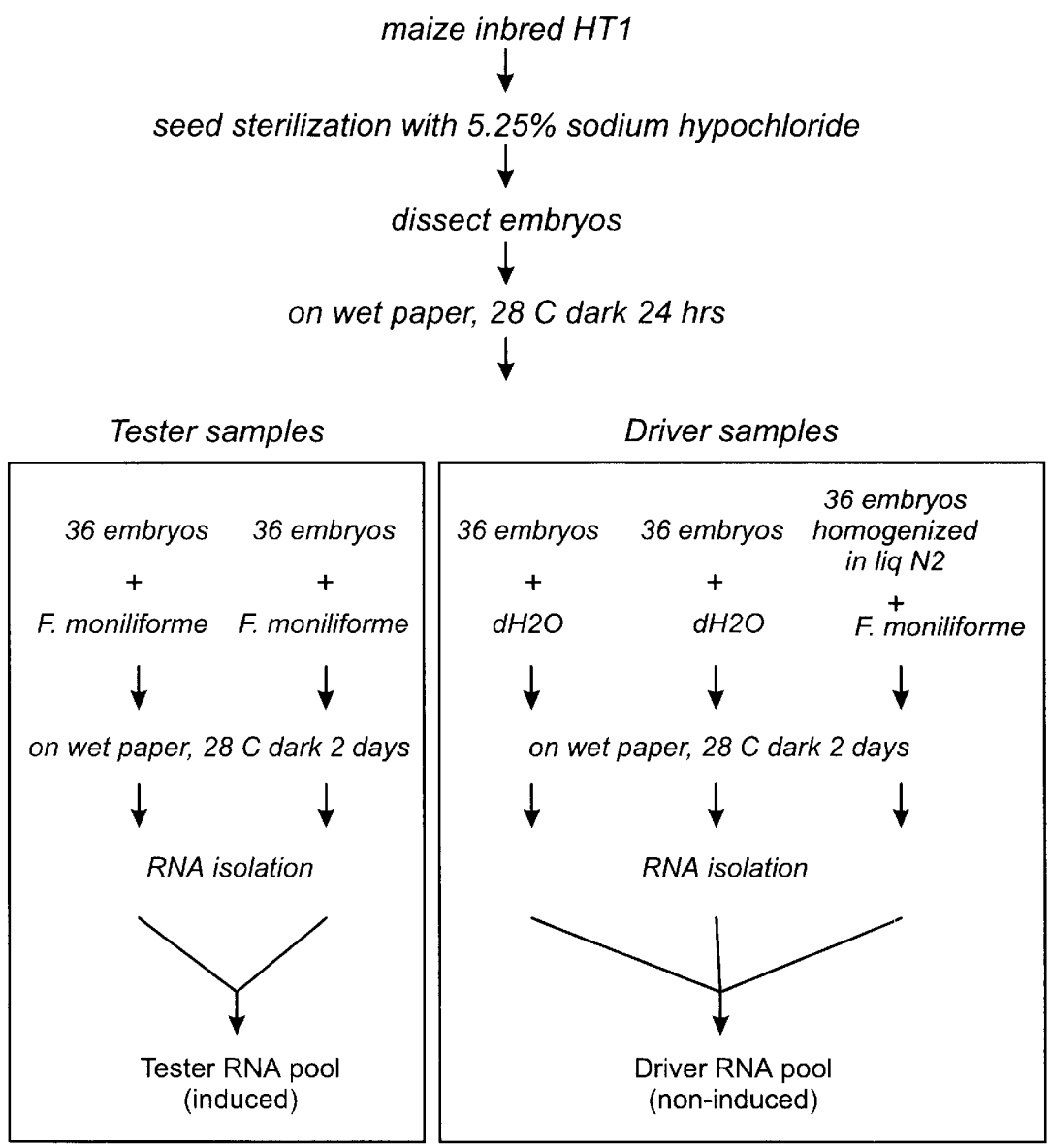
FIG. 4 shows the preparation of tester RNA and of driver RNA for the PCSUB described in Example 1. Here the target cDNA are derived from plant transcripts induced by infection with *Fusarium moniliforme*. Therefore the tester RNA is extracted from *F. monifilorme* infected embryos and driver RNA extracted from embryo RNA+*F. monifilorme* RNA.
Figure 5:
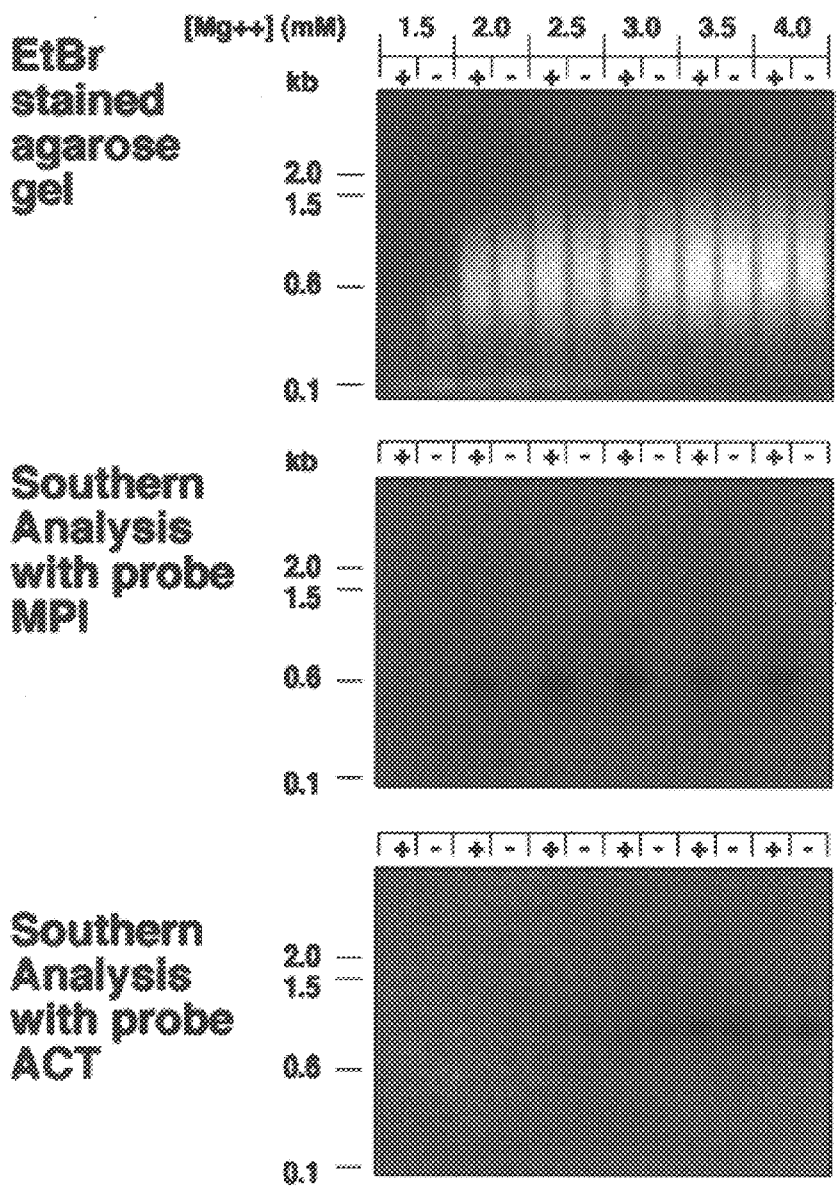
FIG. 5 illustrates the effects of $Mg+^2$ concentration on PCR under conditions employed to amplify the tester (+) and driver (-) cDNA libraries. Top panel shows effect on total cDNA production, as visualized on EtBr stained agarose gel. Mid-panel shows a Southern analysis, using as probe MPI, a gene known to be induced by Fusarium infection. See Cordero et al., *The Plant J.* 6: 141–50 (1994). Bottom panel shows similar analysis with ACT, an actin gene which is not expected to be induced by infection.
Figure 6:
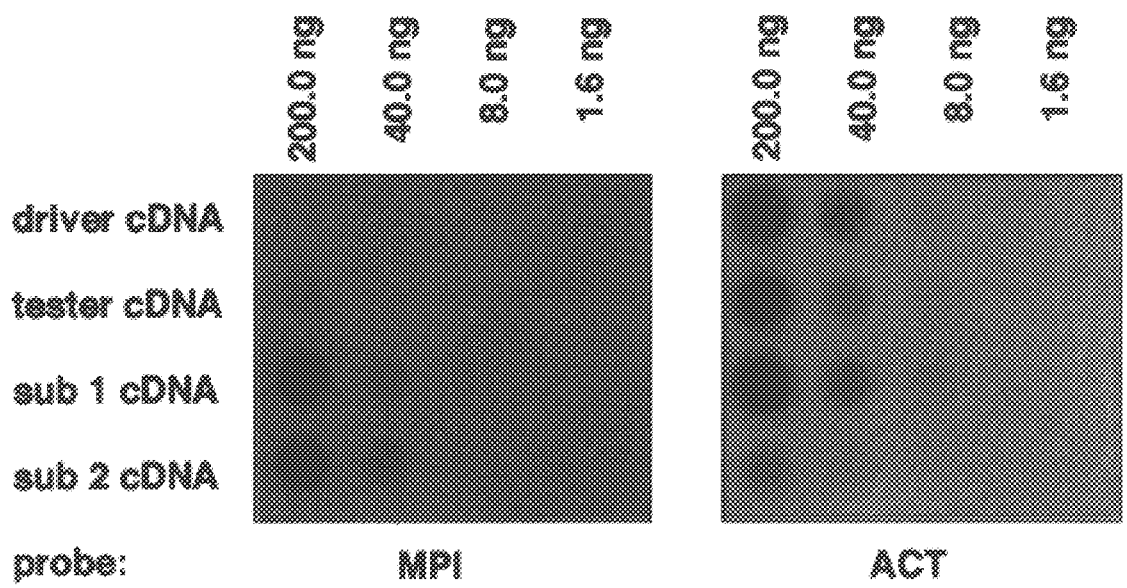
FIG. 6 indicates the effect of each of two rounds of subtractive hybridization between tester and driver cDNA libraries. The left panel is probed with maize protease inhibitor, MPI, a gene expected to be induced by Fusarium infection. The right panel is probed by actin, ACT, a gene expected to be expressed regardless of the infection process.
Figure 7:
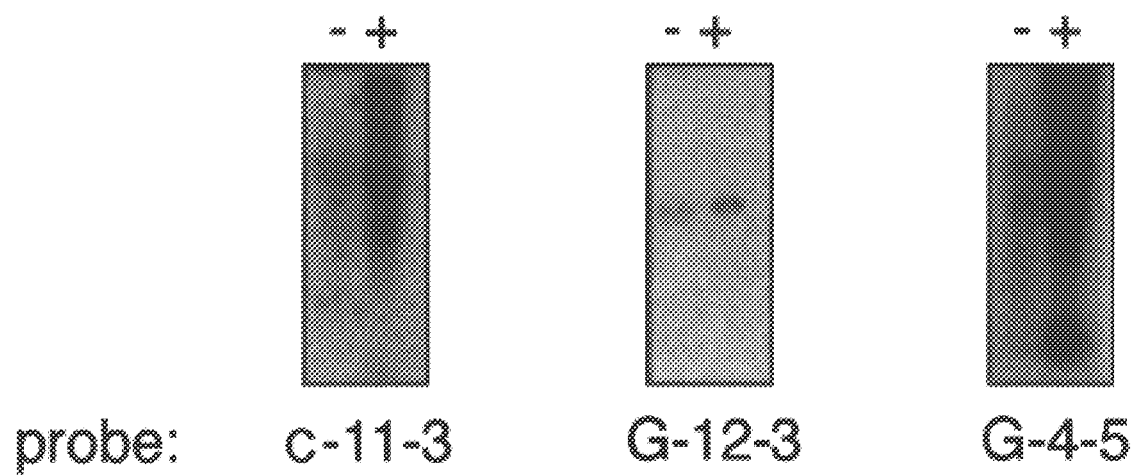
FIG. 7 depicts Northern Analysis of RNA from corn embryo, either induced by infection with the fungus *F. moniliforme* (+) or from uninfected embryos (–). Three clones, (C-11-3, G-12-3 and G-4-5 of Example 1 (SEQ ID NOS:27, 29 and 39, respectively), were fished out from the PCSUB library and were used as probes.

FIG. 4 depicts the preparation of tester and driver RNA pools, some infected embryos (tester RNA) or a mixture of infected embryos and fungus. Total RNA was isolated from infected and non-infected geminating embryos using TriReagent (Molecular Research Center, Inc. Cincinnati, Ohio).

Preparation of cDNA pools with anchored ends

For first strand cDNA synthesis 0.5 μg poly (A)+ RNA was combined with 2 pmoles of BamT17V (mixture of three oligo nucleotides of CGCGGATCCGTTTTTTTTTTTTTTTTTA, CGCGGATC-CGTTTTTTTTTTTTTTTTTTG and CGCGGATC-CGTTTTTTTTTTTTTTTTTC (SEQ ID NOS:13–15, respectively) at equal molar ratio), and DEPC-treated water in a final volume of 11 μl. Mixture was heated at 70° C. for 10 minutes and then chilled on ice for one minute. After addition of 4 μl of 5× first strand cDNA synthesis buffer (Gibco BRL, Gaithersburg, Md.), 1 μl of 10 mM dNTP, 2 μl of 0.1M DTT and 1 μl of placental RNase inhibitor (Promega Corporation, Madison, Wis.), the mixture was incubated at 42° C. for 2 minutes prior to the addition of 1 μl of SuperScript (Gibco BRL, Gaithersburg, Md.). The reaction mixture was further incubated at 42° C. for 30 minutes. After the reaction 2 units of *E. coli* RNase H were added and the mixture was equilibrated at 55° C. for 10 minutes. Primers, unincorporated dNTPs, salts and proteins were removed from first strand cDNAs using GlassMAX™ Spin Cartridges (Gibco BRL) according to the manufacturer's suggestions except the final wash was performed with 400 μl of cold 80% ethanol. First strand of cDNAs were eluted with 150 μl of water (HPLC grade).

The first strand of the cDNA then was tailed with oligo-dC using TdT (Gibco BRL). The reaction mixture contains 36 μl of first strand cDNA, 10 μl of 5× TdT reaction buffer (Gibco BRL), 2 μl of 10 mM dCTP, 2 μl of TdT (10 units/μl). The mixture was incubated at 37° C. for 20 minutes followed by a incubation at 70° C. for 10 minutes. dc-tailed first strand cDNAs (dC-cDNAs) were purified with Glass-MAX™ Spin Cartridges system as described above and eluted with 100 μl water (HPLC grade). dC-cDNAs were amplified using Taq polymerase with primers BamT17V and BamG13H, where primer BamG13H is a mixture of three oligo nucleotides of TAAGGATCCTGGGGGGGGGGGGGA, TAAGGATC-CTGGGGGGGGGGGGGGT and TAAGGATC-CTGGGGGGGGGGGGGGC (SEQ ID NOS:16–18, respectively) at equal molar ratio. The reaction contained 2 µl of dC-cDNA in a final volume of 50 µl 1× amplification buffer [20 mM Tris-HCl (pH 7.3), 50 mM KCl, 3.0 mM $MgCl^2$, 1 µM of each primer, 0.4 mM dNTP]. The mixture was overlaid with 60 µl light mineral oil and placed into a 96-well format MJ Thermal Cycler. The reaction mixture was heated at 94° C. for 4 minutes then the temperature was held at 72° C. during addition of 1 unit Taq polymerase (Boehringer Mannheim Corporation). PCR conditions were as follows: 25 cycles of 94° C. for 30 seconds, 60° C. for 30 seconds, and 72° C. for 5 minutes. After the final cycle the mixture was further incubated at 72° C. for additional 10 minutes. The amplified "anchored" cDNAs (SEQ ID NOS:16–18, 21–23, 24–26 and 13–15, respectively) (FIG. 1) were purified with GeneClean (Bio 101, Vista, Calif.). Subtractive cloning of cDNAs from genes that are induced upon infection by *Fusarium moniliforme* in germinating embryos of maize Tester RNA were isolated from 72 Fusarium infected geminating embryos. To prepare driver RNA, 36 embryos were homogenized in liquid nitrogen and inoculated with *Fusarium moniliforme.* The resulting materials were combined with 72 non-infected geminating embryos to generate a driver RNA pool. For driver dC-cDNA amplification, a final 16 μM biotin-14-dCTP (Gibco BRL, Gaithersburg, Md.) was included to label driver cDNAs. Both driver and tester cDNAs were amplified with BamT17V and BamG13H primers as described in the previous section.

Subtraction was modified from Lisitsyn et al., supra. For each cycle of subtraction, 4–10 μg of tester cDNAs or the subtractive cDNAs (from previous cycle of subtraction) were digested with BamHI (100–200 units) at 37° C. for four hours. Then the proteins were removed by phenol and phenol/chloroform extraction. DNA was precipitated with ethanol. 2 μg of the resulting DNA was ligated to an adapter in a final volume of 60 μl: 16.7 mM 24-mer oligo, 16.7 mM 12-mer oligo 1× T4 DNA ligase buffer (New England BioLabs, Inc.). The mixture was heated at 55° C. for 10 minutes and then slowly cooled down to 10° C. (about 1 hour). After addition of 800 units T4 DNA ligase (New England BioLabs, Inc.) the reaction mixture was incubated at 16° C. for 20 hours. The three pairs of adapters used in successive rounds of subtraction were as described in the table above.

For tester cDNA and driver cDNA hybridization 0.4 μg of the resulting tester cDNA was mixed with 40 μg of biotin labeled driver cDNA and the DNA mixture was precipitated with ethanol. After centrifugation DNA pellet was washed twice with 70% ethanol and air dried. The pellet was resuspended in 4 μl of EE×3 buffer (30 mM EPPS from Sigma, pH 8.0 at 20° C., 3 mM EDTA) by vortexing for 2–5 minutes. The mixture was overlaid with 35 μl mineral oil and then heated at 98° C. for 4 minutes during addition of 1 μl 5M NaCl, followed by a 67° C. incubation for 20–40 hours. After the hybridization 500 μl of water (HPLC grade) and 150 μl chloroform were added to the DNA drop. The aqueous phase was transferred to a new tube.

To remove biotin labeled-DNA and the DNAs associated with them, 3 mg Streptavidin-Paramagnetic Particles in 0.5 ml 1× SSC (Promega Corporation) was added to the driver-tester cDNA hybridization solution and mixture was incubated at room temperature for 20 minutes. Then the Streptavidin-Paramagnetic Particles were captured with a Magnetic Stand (Promega Corporation). After a brief centrifugation the DNA in the supernatant (subtractive cDNA) was isolated with GeneClean system (Bio 101) in a final volume of 150 μl.

Two microliters of the subtractive cDNAs were filled in and amplified in a final volume of 50 μl [20 mM Tris-HCl (pH 7.3), 50 mM KCl, 3.0 mM $MgCl^2$, 1 μM of the corresponding 24-mer primer (R Bam24, J Bam 24, or N Bam 24), 0.4 mM dNTP]. The mixture was mixed with 2 units of Taq polymerase at 72° C. and incubated further at 72° C. for 20 minutes. The resulting DNAs were amplified at following condition: 23 cycles of 94° C. for 30 seconds, 65° C. for 30 seconds, and 72° C. for 5 minutes. After the final cycle the mixture was further incubated at 72° C. for additional 10 minutes. After digestion with BamHI, the amplified subtractive DNA was either subjected the next round of subtraction (for the first two rounds of subtractive cDNA) or cloned into BamHI digested, dephosphoralated pBlueScript vector (for the third round of subtractive cDNA).

PCR conditions for amplification of "anchored" library were optimized. The results indicated that $Mg^{2+}$ concentration was crucial for success of amplification of such cDNA library (FIG. 5). As demonstrated in FIG. 5, 2.5 mM $Mg^{2+}$ seems to be the best concentration.

In order to evaluate the performance of this technique, maize proteinase inhibitor (MPI) cDNA and maize actin (ACT) cDNA fragments were used as probes to analyze subtractive cDNA pools at the end of each subtraction cycle. An analysis of the results indicated that actin cDNA, a cDNA presents equally in both libraries, was removed at the end of the second round procedure. MPI is a cDNA from a gene that was activated upon infection of maize germinating embryos by *Fusarium moniliforme* (Cordero et al., supra), and was enriched about 25- to 50-fold (FIG. 6).

Pursuant to the above-described procedure, cDNA clones designated C-11-3, G-4-5 and G-12-3 (SEQ ID NOS:27, 29 and 39, respectively) were obtained to exemplify genes that are activated upon *F. moniliforme* infection of germinating maize embryos. Northern blot analysis using these cDNAs as probes indicated that the genes are activated during infection (FIG. 7). Sequence analysis of these clones indicated that they are novel cDNA's. DNA database search result suggested that G-12-3 (SEQ ID NO:39) may code for a cytochrome P450 protein (FIG. 10). Clone C-11-3 (SEQ ID NO:27) (FIG. 8) and G-4-5 (SEQ ID NO:29) (FIG. 9) did not match up any known sequences in database.

FIG. 11 shows how the sequence information on clone G-12-3 was applied to the ICEFAL technique, resulting in the isolation of the 5'-end of the gene. The primers used were GSP1 (SEQ ID NO:19) and GSP2 (SEQ ID NO:20), which have the sequences 5'-CCGCTCTTACTCCGTTCAGTCTTG-3' and 5'-CCATTCCCTTCAATCACCCATTTC-3', respectively.

What is claimed is:

1. A method for generating and screening a cDNA library with anchored ends, comprising the steps of
   (a) providing an RNA preparation that comprises polyadenylated mRNA from a biological sample, said polyadenylated mRNA having a polyA portion and a non-polyA portion;
   (b) preparing a first oligonucleotide primer that anneals to said polyA portion of said polyadenylated mRNA, anchoring said first primer such that a reverse transcriptase reaction can start within one nucleotide from the 3' end of said non-polyA portion;
   (c) contacting said first primer to generate by PCR from said RNA preparation DNA strands that are complementary to said polyadenylated mRNA;
   (d) adding a polynucleotide tail at the 3' end of said DNA strands by terminal deoxynucleotidyl transferase, whereby said DNA strands have a first portion that is complementary to said polyadenylated mRNA and a tail portion;
   (e) preparing a second oligonucleotide primer that anneals to said polynucleotide tail attached in step (d), anchoring said second primer such that a reverse transcriptase reaction can start one nucleotide downstream from the 5' end of said first portion of said DNA strands;
   (f) contacting said first primer and said second primer to amplify said DNA strands by PCR and produce a cDNA library with anchored ends; and
   (g) screening said cDNA library with anchored ends without the necessity of cloning and propagating said library in a recombinant host system.

2. A method of generating a cDNA library with anchored ends as claimed in claim 1, wherein said polynucleotide added by using terminal deoxynucleotidyl transferase in step (d) is a polyC tail, and said second oligonucleotide primer prepared in step (e) is a polyGH primer.

3. A method of generating a cDNA library with anchored ends as claimed in claim 1, wherein each of said first primer and said second primer contains a recognition site for a restriction endonuclease.

4. A method of isolating a cDNA end of a unique cDNA from an anchored library produced according to claim 1, comprising the steps
   (a) providing an additional PCR primer that hybridizes to a sequence internal to said unique cDNA, and
   (b) using said additional primer with said first or said second primer in PCR reactions to produce an end of said cDNA,
wherein, optionally, all said primers in steps (a) and (b) contain at least one restriction enzyme cleavage site.

* * * * *

UNITED STATES PATENT AND TRADEMARK OFFICE
CERTIFICATE OF CORRECTION

PATENT NO. : 5,837,468
DATED : Nov. 17, 1998
INVENTOR(S) : Wang et al.

It is certified that error appears in the above-identified patent and that said Letters Patent is hereby corrected as shown below:

On the title page item [54],

In the title, "CDNA SUBSTRACTIVE" should read --cDNA SUBTRACTIVE--.

On the title page item [56],

In the References Cited, Other Publications, line 2, "Luk'Tanov" should read --Luk'Yanov--.
In the References Cited, Other Publications, line 6, "3+" should read --3'--.

Signed and Sealed this

Twenty-seventh Day of April, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGCACTCTCC AGCCTCTCAC CGAG        24

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GATCCTCGGT GA        12

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGCACTCTCC AGCCTCTCAC CGAG        24

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GATCCTCGGT GA        12

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ACCGACGTCG ACTATCCATG AACG        24

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATCCGTTCA TG                                                                                              12

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ACCGACGTCG ACTATCCATG AACG                                                                                 24

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GATCCGTTCA TG                                                                                              12

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AGGCAACTGT GCTATCCGAG GGAG                                                                                 24

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GATCCTCCCT CG                                                                                              12

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

AGGCAACTGT GCTATCCGAG GGAG                                                                                 24

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GATCCTCCCT CG 12

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:13:

CGCGGATCCG TTTTTTTTT TTTTTTTA 28

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:14:

CGCGGATCCG TTTTTTTTT TTTTTTG 28

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:15:

CGCGGATCCG TTTTTTTTT TTTTTTC 28

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:16:

TAAGGATCCT GGGGGGGGGG GGGA 24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:17:

TAAGGATCCT GGGGGGGGGG GGGT 24

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

TAAGGATCCT GGGGGGGGGG GGGC 24

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CCGCTCTTAC TCCGTTCAGT CTTG     24

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CCATTCCCTT CAATCACCCA TTTC     24

( 2 ) INFORMATION FOR SEQ ID NO:21:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GCGCCTAGGC AAAAAAAAA AAAAAAAT     28

( 2 ) INFORMATION FOR SEQ ID NO:22:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCGCCTAGGC AAAAAAAAA AAAAAAAG     28

( 2 ) INFORMATION FOR SEQ ID NO:23:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCGCCTAGGC AAAAAAAAA AAAAAAAC     28

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

ATTCCTAGGA CCCCCCCCCC CCCT     24

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
ATTCCTAGGA  CCCCCCCCCC  CCCA                                          24
```

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
ATTCCTAGGA  CCCCCCCCCC  CCCG                                          24
```

( 2 ) INFORMATION FOR SEQ ID NO:27:

( i ) SEQUENCE CHARACTERISTICS:
        ( A ) LENGTH: 486 base pairs
        ( B ) TYPE: nucleic acid
        ( C ) STRANDEDNESS: single
        ( D ) TOPOLOGY: linear ( i x ) FEATURE:
        ( A ) NAME/KEY: mat_peptide
        ( B ) LOCATION: 68..364

( i x ) FEATURE:
        ( A ) NAME/KEY: CDS
        ( B ) LOCATION: 68..364

( x i ) SEQUENCE DESCRIPTION: SEQ ID NO:27:

```
GGATCCTGGG  GGGGGGGGGA  CGAACTCTCT  CTATACTCTC  CCATCAATCC  TTAAATTATC       60

ACGCATT ATG CGA ACT GTT GCA GTA CTC GCT CTC TTT GCC CAA CTG GCG            109
        Met Arg Thr Val Ala Val Leu Ala Leu Phe Ala Gln Leu Ala
        1           5                       10

ACG TGC GCC ATA TTC AAC ATC ACA GGA TCG TGC GCC GAC AGC GAA AAC            157
Thr Cys Ala Ile Phe Asn Ile Thr Gly Ser Cys Ala Asp Ser Glu Asn
15              20              25                  30

GGC CCT GTT TGC GTC ATT ACG AAG AGT GTA GTT AAC CCA GCT ACA GTT            205
Gly Pro Val Cys Val Ile Thr Lys Ser Val Val Asn Pro Ala Thr Val
            35              40              45

TGC AAC GGG AAG GCT GAG GCG TAT GCA GGA GAC GGG AAT CAA TGG CAT            253
Cys Asn Gly Lys Ala Glu Ala Tyr Ala Gly Asp Gly Asn Gln Trp His
        50              55              60

GAC GGG CTG TAC TGG AAT TGG TTC CCC TTG CAC TTA TGT TTG GCG ATG            301
Asp Gly Leu Tyr Trp Asn Trp Phe Pro Leu His Leu Cys Leu Ala Met
        65              70              75

CTA GAC GTT CTT CCT CAA CAT CAA ACT GCG AAG ACA CTG AAT TCG CTT            349
Leu Asp Val Leu Pro Gln His Gln Thr Ala Lys Thr Leu Asn Ser Leu
    80              85              90

TCG GAC CTT GGT ATA TAATCAGCTG CAGGTCCTGG CCTACTCCCT GTTCAACTAA            404
Ser Asp Leu Gly Ile
95

AAGCAACATT  GCTTTCGTTT  GTCTTCCTGT  ATTACCATCA  ATCAGAATTA  ACATACTCAT      464

CTCTTAAAAA  AAAAAAAAAA  AA                                                  486
```

( 2 ) INFORMATION FOR SEQ ID NO:28:

(i) SEQUENCE CHARACTERISTICS:
    (A) LENGTH: 99 amino acids
    (B) TYPE: amino acid
    (D) TOPOLOGY: linear (ii) MOLECULE TYPE: protein (xi) SEQUENCE DESCRIPTION: SEQ ID NO:28:

```
Met Arg Thr Val Ala Val Leu Ala Leu Phe Ala Gln Leu Ala Thr Cys
 1               5                  10                  15

Ala Ile Phe Asn Ile Thr Gly Ser Cys Ala Asp Ser Glu Asn Gly Pro
                20                  25                  30

Val Cys Val Ile Thr Lys Ser Val Val Asn Pro Ala Thr Val Cys Asn
            35                  40                  45

Gly Lys Ala Glu Ala Tyr Ala Gly Asp Gly Asn Gln Trp His Asp Gly
        50                  55                  60

Leu Tyr Trp Asn Trp Phe Pro Leu His Leu Cys Leu Ala Met Leu Asp
 65                  70                  75                  80

Val Leu Pro Gln His Gln Thr Ala Lys Thr Leu Asn Ser Leu Ser Asp
                    85                  90                  95

Leu Gly Ile
```

(2) INFORMATION FOR SEQ ID NO:29:

(i) SEQUENCE CHARACTERISTICS:
    (A) LENGTH: 471 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: join(1..111, 115..255, 259..270, 274..321, 325
        ..342, 346..402, 406..471)

(xi) SEQUENCE DESCRIPTION: SEQ ID NO:29:

```
GTG GAT CCT TCG ACG ACT ACC GCA TGT ACA TCC GCC GCA AGG GGC CTC     48
Val Asp Pro Ser Thr Thr Thr Ala Cys Thr Ser Ala Ala Arg Gly Leu
 1               5                  10                  15

GCG GGA AGA GCC AGG TCG ACT CCC TCA AGG TCG CCG ACG CCG ACG GCA     96
Ala Gly Arg Ala Arg Ser Thr Pro Ser Arg Ser Pro Thr Pro Thr Ala
                20                  25                  30

GAC AGT GCT ACT AGC TAG TAT ATA CCT AGC CAG CCT GCT GCC GAT CGA    144
Asp Ser Ala Thr Ser     Tyr Ile Pro Ser Gln Pro Ala Ala Asp Arg
            35                  40                  45

GAT TGT TTG TAT GTG TGG TGT GTG CAT GCA TTT GCC CAC ACT GAC CAC    192
Asp Cys Leu Tyr Val Trp Cys Val His Ala Phe Ala His Thr Asp His
        50                  55                  60

TGT CCA CAT GTA CGC CGC CAG CTG CCG GCC CTA AAT AAA ACC ATG CAT    240
Cys Pro His Val Arg Arg Gln Leu Pro Ala Leu Asn Lys Thr Met His
 65                  70                  75

AGA TTA GCT AGC TTA TGA TTA ATC AAG TCT TAG CAG CTA GAG AGT GCT    288
Arg Leu Ala Ser Leu     Leu Ile Lys Ser     Gln Leu Glu Ser Ala
 80                          85                  90

TTG GGT TGG GAC TCT CTC ATA GGA GGG NAT GCT TGA TCG ATC CGA TCA    336
Leu Gly Trp Asp Ser Leu Ile Gly Gly Xaa Ala     Ser Ile Arg Ser
        95                  100                 105

TCA ATT TGA AAC ACC CTG CTA GGT TGT GCA NCT CCG CCG TCC AAN CCA    384
Ser Ile     Asn Thr Leu Leu Gly Cys Ala Xaa Pro Pro Ser Xaa Pro
     110                     115                 120

CAA AGG GGN GAN GTC AAN TGA AGG GTG AGA NAA CGT CAA NAA CGA AGC    432
Gln Arg Xaa Xaa Val Xaa     Arg Val Arg Xaa Arg Gln Xaa Arg Ser
```

|     |     |     |     |     |     |     |     |     |     |     |     |     |
|-----|-----|-----|-----|-----|-----|-----|-----|-----|-----|-----|-----|-----|
|     | 125 |     |     |     | 130 |     |     |     | 135 |     |     |     |
| NAG | CTA | GTT | CCC | NTT | ATT | NGG | GTG | GTT | CTC | AAA | AAA | AAA |
| Xaa | Leu | Val | Pro | Xaa | Ile | Xaa | Val | Val | Leu | Lys | Lys | Lys |
|     | 140 |     |     |     | 145 |     |     |     | 150 |     |     |     |

471

( 2 ) INFORMATION FOR SEQ ID NO:30:

( i ) SEQUENCE CHARACTERISTICS:
    ( A ) LENGTH: 151 amino acids
    ( B ) TYPE: amino acid
    ( D ) TOPOLOGY: linear ( i i ) MOLECULE TYPE: protein ( x i ) SEQUENCE DESCRIPTION: SEQ ID NO:30:

```
Val  Asp  Pro  Ser  Thr  Thr  Thr  Ala  Cys  Thr  Ser  Ala  Ala  Arg  Gly  Leu
 1                   5                        10                       15

Ala  Gly  Arg  Ala  Arg  Ser  Thr  Pro  Ser  Arg  Ser  Pro  Thr  Pro  Thr  Ala
                20                       25                       30

Asp  Ser  Ala  Thr  Ser  Tyr  Ile  Pro  Ser  Gln  Pro  Ala  Ala  Asp  Arg  Asp
           35                        40                       45

Cys  Leu  Tyr  Val  Trp  Cys  Val  His  Ala  Phe  Ala  His  Thr  Asp  His  Cys
      50                        55                       60

Pro  His  Val  Arg  Arg  Gln  Leu  Pro  Ala  Leu  Asn  Lys  Thr  Met  His  Arg
 65                       70                       75                        80

Leu  Ala  Ser  Leu  Leu  Ile  Lys  Ser  Gln  Leu  Glu  Ser  Ala  Leu  Gly  Trp
                     85                       90                       95

Asp  Ser  Leu  Ile  Gly  Gly  Xaa  Ala  Ser  Ile  Arg  Ser  Ser  Ile  Asn  Thr
                100                      105                      110

Leu  Leu  Gly  Cys  Ala  Xaa  Pro  Pro  Ser  Xaa  Pro  Gln  Arg  Xaa  Xaa  Val
           115                      120                      125

Xaa  Arg  Val  Arg  Xaa  Arg  Gln  Xaa  Arg  Ser  Xaa  Leu  Val  Pro  Xaa  Ile
130                      135                      140

Xaa  Val  Val  Leu  Lys  Lys  Lys
145                      150
```

( 2 ) INFORMATION FOR SEQ ID NO:31:

( i ) SEQUENCE CHARACTERISTICS:
    ( A ) LENGTH: 148 amino acids
    ( B ) TYPE: amino acid
    ( C ) STRANDEDNESS: single
    ( D ) TOPOLOGY: linear ( x i ) SEQUENCE DESCRIPTION: SEQ ID NO:31:

```
Trp  Ile  Leu  Arg  Arg  Leu  Pro  His  Val  His  Pro  Pro  Gln  Gly  Ala  Ser
 1                    5                       10                      15

Arg  Glu  Glu  Pro  Gly  Arg  Leu  Pro  Gln  Gly  Arg  Arg  Arg  Arg  Arg  Gln
                20                       25                       30

Thr  Val  Leu  Leu  Ala  Ser  Ile  Tyr  Leu  Ala  Ser  Leu  Leu  Pro  Ile  Glu
            35                       40                       45

Ile  Val  Cys  Met  Cys  Gly  Val  Cys  Met  His  Leu  Pro  Thr  Leu  Thr  Thr
       50                       55                       60

Val  His  Met  Tyr  Ala  Ala  Ser  Cys  Arg  Pro  Ile  Lys  Pro  Cys  Ile  Asp
 65                       70                       75                       80

Leu  Ala  Tyr  Asp  Ser  Ser  Leu  Ser  Ser  Arg  Val  Leu  Trp  Val  Gly  Thr
                     85                       90                       95

Leu  Ser  Glu  Gly  Met  Leu  Asp  Arg  Ser  Asp  His  Gln  Phe  Glu  Thr  Pro
                100                      105                      110
```

```
Cys  Val  Val  Xaa  Leu  Arg  Arg  Pro  Xaa  His  Lys  Gly  Xaa  Xaa  Ser  Xaa
          115                      120                     125

Glu  Gly  Xaa  Asn  Val  Xaa  Asn  Glu  Ala  Ser  Phe  Pro  Leu  Xaa  Gly  Trp
          130                     135                     140

Phe  Ser  Lys  Lys
145
```

( 2 ) INFORMATION FOR SEQ ID NO:32:

( i ) SEQUENCE CHARACTERISTICS:
         ( A ) LENGTH: 150 amino acids
         ( B ) TYPE: amino acid
         ( C ) STRANDEDNESS: single
         ( D ) TOPOLOGY: linear ( x i ) SEQUENCE DESCRIPTION: SEQ ID NO:32:

```
Gly  Ser  Phe  Asp  Asp  Tyr  Arg  Met  Tyr  Ile  Arg  Arg  Lys  Gly  Pro  Arg
1                   5                        10                       15

Gly  Lys  Ser  Gln  Val  Asp  Ser  Leu  Lys  Val  Ala  Asp  Ala  Asp  Gly  Arg
               20                      25                      30

Gln  Cys  Tyr  Leu  Val  Tyr  Thr  Pro  Ala  Cys  Cys  Arg  Ser  Arg  Leu  Phe
               35                      40                      45

Val  Cys  Val  Val  Cys  Ala  Cys  Ile  Cys  Pro  His  Pro  Leu  Ser  Thr  Cys
     50                      55                      60

Thr  Pro  Pro  Ala  Ala  Gly  Pro  Lys  Asn  His  Ala  Ile  Ser  Leu  Met  Ile
65                       70                      75                       80

Asn  Gln  Val  Leu  Ala  Ala  Arg  Glu  Cys  Phe  Gly  Leu  Gly  Leu  Ser  His
                    85                      90                      95

Arg  Arg  Xaa  Cys  Leu  Ile  Asp  Pro  Ile  Ile  Asn  Leu  Lys  His  Pro  Ala
               100                     105                     110

Arg  Leu  Cys  Xaa  Ser  Ala  Val  Gln  Xaa  Thr  Lys  Gly  Xaa  Xaa  Gln  Xaa
               115                     120                     125

Lys  Gly  Glu  Xaa  Thr  Ser  Xaa  Thr  Lys  Xaa  Ala  Ser  Ser  Xaa  Tyr  Xaa
          130                     135                     140

Gly  Gly  Ser  Gln  Lys  Lys
145                     150
```

( 2 ) INFORMATION FOR SEQ ID NO:33:

( i ) SEQUENCE CHARACTERISTICS:
         ( A ) LENGTH: 83 amino acids
         ( B ) TYPE: amino acid
         ( C ) STRANDEDNESS: single
         ( D ) TOPOLOGY: linear ( x i ) SEQUENCE DESCRIPTION: SEQ ID NO:33:

```
Glu  Arg  Tyr  Asn  Pro  Gln  Arg  Trp  Leu  Asp  Ile  Arg  Gly  Ser  Gly  Arg
1                   5                        10                       15

Asn  Phe  His  His  Val  Pro  Phe  Gly  Phe  Gly  Met  Arg  Gln  Cys  Leu  Gly
               20                      25                      30

Arg  Arg  Leu  Ala  Glu  Val  Glu  Met  Leu  Leu  Leu  Leu  His  His  Val  Leu
               35                      40                      45

Lys  His  Phe  Leu  Val  Glu  Thr  Leu  Thr  Gln  Glu  Asp  Ile  Lys  Met  Val
          50                      55                      60

Tyr  Ser  Phe  Ile  Leu  Arg  Pro  Gly  Thr  Ser  Pro  Leu  Leu  Thr  Phe  Arg
65                       70                      75                       80

Ala  Ile  Asn
```

( 2 ) INFORMATION FOR SEQ ID NO:34:

( i ) SEQUENCE CHARACTERISTICS:
    ( A ) LENGTH: 83 amino acids
    ( B ) TYPE: amino acid
    ( C ) STRANDEDNESS: single
    ( D ) TOPOLOGY: linear ( x i ) SEQUENCE DESCRIPTION: SEQ ID NO:34:

| Glu | Arg | Tyr | Asn | Pro | Gln | Arg | Trp | Leu | Asp | Ile | Arg | Gly | Ser | Gly | Arg |
|---|---|---|---|---|---|---|---|---|---|---|---|---|---|---|---|
| 1 | | | | 5 | | | | | 10 | | | | | 15 | |
| Asn | Phe | His | His | Val | Pro | Phe | Gly | Phe | Gly | Met | Arg | Gln | Cys | Leu | Gly |
| | | | 20 | | | | 25 | | | | | | 30 | | |
| Arg | Arg | Leu | Ala | Glu | Ala | Glu | Met | Leu | Leu | Leu | Leu | His | His | Val | Leu |
| | | 35 | | | | | 40 | | | | | 45 | | | |
| Lys | His | Phe | Leu | Val | Glu | Thr | Leu | Thr | Gln | Glu | Asp | Ile | Lys | Met | Val |
| | | 50 | | | | | 55 | | | | | 60 | | | |
| Tyr | Ser | Phe | Ile | Leu | Arg | Pro | Gly | Thr | Ser | Pro | Leu | Leu | Thr | Phe | Arg |
| 65 | | | | | 70 | | | | | 75 | | | | | 80 |
| Ala | Ile | Asn | | | | | | | | | | | | | |

( 2 ) INFORMATION FOR SEQ ID NO:35:

( i ) SEQUENCE CHARACTERISTICS:
        ( A ) LENGTH: 86 amino acids
        ( B ) TYPE: amino acid
        ( C ) STRANDEDNESS: single
        ( D ) TOPOLOGY: linear ( x i ) SEQUENCE DESCRIPTION: SEQ ID NO:35:

| Glu | Lys | Phe | Asp | Pro | Gly | His | Phe | Leu | Asn | Ala | Asn | Gly | Thr | Phe | Arg |
|---|---|---|---|---|---|---|---|---|---|---|---|---|---|---|---|
| 1 | | | | 5 | | | | | 10 | | | | | 15 | |
| Lys | Ser | Asn | Tyr | Phe | Met | Pro | Phe | Ser | Ala | Gly | Lys | Arg | Ile | Cys | Ala |
| | | | 20 | | | | 25 | | | | | | 30 | | |
| Gly | Glu | Gly | Leu | Ala | Arg | Met | Glu | Leu | Phe | Leu | Phe | Leu | Thr | Ser | Ile |
| | | 35 | | | | | 40 | | | | | 45 | | | |
| Leu | Gln | Asn | Phe | Ser | Leu | Lys | Pro | Val | Lys | Asp | Arg | Lys | Asp | Ile | Asp |
| | | 50 | | | | | 55 | | | | | 60 | | | |
| Ile | Ser | Pro | Ile | Val | Thr | Ser | Ala | Ala | Asn | Ile | Pro | Arg | Pro | Tyr | Glu |
| 65 | | | | | 70 | | | | | 75 | | | | | 80 |
| Val | Ser | Phe | Ile | Pro | Arg | | | | | | | | | | |
| | | | | 85 | | | | | | | | | | | |

( 2 ) INFORMATION FOR SEQ ID NO:36:

( i ) SEQUENCE CHARACTERISTICS:
        ( A ) LENGTH: 86 amino acids
        ( B ) TYPE: amino acid
        ( C ) STRANDEDNESS: single
        ( D ) TOPOLOGY: linear ( x i ) SEQUENCE DESCRIPTION: SEQ ID NO:36:

| Glu | Lys | Phe | Asp | Pro | Gly | His | Phe | Leu | Asn | Ala | Asn | Gly | Thr | Phe | Arg |
|---|---|---|---|---|---|---|---|---|---|---|---|---|---|---|---|
| 1 | | | | 5 | | | | | 10 | | | | | 15 | |
| Arg | Ser | Asp | Tyr | Phe | Met | Pro | Phe | Ser | Ala | Gly | Lys | Arg | Ile | Cys | Ala |
| | | | 20 | | | | 25 | | | | | | 30 | | |
| Gly | Glu | Gly | Leu | Ala | Arg | Met | Glu | Ile | Phe | Leu | Phe | Leu | Thr | Ser | Ile |
| | | 35 | | | | | 40 | | | | | 45 | | | |
| Leu | Gln | Asn | Phe | Ser | Leu | Lys | Pro | Val | Lys | Asp | Arg | Lys | Asp | Ile | Asp |
| | | 50 | | | | | 55 | | | | | 60 | | | |
| Ile | Ser | Pro | Ile | Ile | Thr | Ser | Leu | Ala | Asn | Met | Pro | Arg | Pro | Tyr | Glu |
| 65 | | | | | 70 | | | | | 75 | | | | | 80 |

```
Val  Ser  Phe  Ile  Pro  Arg
                    85
```

(2) INFORMATION FOR SEQ ID NO:37:

(i) SEQUENCE CHARACTERISTICS:
        (A) LENGTH: 86 amino acids
        (B) TYPE: amino acid
        (C) STRANDEDNESS: single
        (D) TOPOLOGY: linear (xi) SEQUENCE DESCRIPTION: SEQ ID NO:37:

```
Gln  Asp  Phe  Asn  Pro  Gln  His  Phe  Leu  Asn  Glu  Lys  Gly  Gln  Phe  Lys
1                   5                        10                       15
Lys  Ser  Asp  Ala  Phe  Val  Pro  Phe  Ser  Ile  Gly  Lys  Arg  Asn  Cys  Phe
               20                       25                       30
Gly  Glu  Gly  Leu  Ala  Arg  Met  Glu  Leu  Phe  Leu  Phe  Phe  Thr  Thr  Val
          35                            40                       45
Met  Gln  Asn  Phe  Arg  Leu  Lys  Ser  Ser  Gln  Ser  Pro  Lys  Asp  Ile  Asp
     50                       55                       60
Val  Ser  Pro  Lys  His  Val  Gly  Phe  Ala  Thr  Ile  Pro  Arg  Asn  Tyr  Thr
65                       70                       75                            80
Met  Ser  Phe  Leu  Pro  Arg
                    85
```

(2) INFORMATION FOR SEQ ID NO:38:

(i) SEQUENCE CHARACTERISTICS:
        (A) LENGTH: 87 amino acids
        (B) TYPE: amino acid
        (C) STRANDEDNESS: single
        (D) TOPOLOGY: linear (xi) SEQUENCE DESCRIPTION: SEQ ID NO:38:

```
Glu  Thr  Phe  Lys  Pro  Glu  His  Phe  Leu  Asn  Glu  Asn  Gly  Lys  Phe  Lys
1                   5                        10                       15
Tyr  Ser  Asp  Tyr  Phe  Lys  Ala  Phe  Ser  Ala  Gly  Lys  Arg  Val  Cys  Val
               20                       25                       30
Gly  Glu  Gly  Leu  Ala  Arg  Met  Glu  Leu  Phe  Leu  Leu  Leu  Ser  Ala  Ile
          35                            40                       45
Leu  Gln  His  Phe  Asn  Leu  Lys  Ser  Leu  Val  Asp  Pro  Lys  Asp  Ile  Asp
     50                       55                       60
Leu  Ser  Pro  Val  Thr  Ile  Gly  Phe  Gly  Ser  Ile  Pro  Arg  Glu  Phe  Val
65                       70                       75                            80
Ile  Cys  Val  Ile  Pro  Arg  Ser
                    85
```

(2) INFORMATION FOR SEQ ID NO:39:

(i) SEQUENCE CHARACTERISTICS:
        (A) LENGTH: 87 amino acids
        (B) TYPE: amino acid
        (C) STRANDEDNESS: single
        (D) TOPOLOGY: linear (xi) SEQUENCE DESCRIPTION: SEQ ID NO:39:

```
Glu  Lys  Phe  Ile  Pro  Glu  Arg  Trp  Leu  Asn  Glu  Thr  Pro  Glu  Met  Lys
1                   5                        10                       15
Ser  Ala  Leu  Thr  Pro  Phe  Ser  Leu  Gly  Lys  Arg  Asn  Cys  Ile  Gly  Gln
               20                       25                       30
Asn  Leu  Ala  Trp  Gln  Glu  Leu  Tyr  Trp  Ala  Val  Asn  Glu  Val  Met  Arg
```

-continued

```
                35                            40                            45
Ser  Gly  Ser  Arg  Phe  Arg  Val  Ala  Glu  Glu  Met  Lys  Asp  Trp  Glu  Met
     50                       55                      60

Glu  Met  Glu  Asp  Arg  Phe  Asn  Ile  Ala  Pro  Arg  Gly  Arg  Arg  Leu  Met
65                       70                       75                       80

Leu  Thr  Ala  Ser  Gln  Val  Asn
                    85
```